United States Patent [19]  [11] Patent Number: 4,751,133
Szycher et al.  [45] Date of Patent: Jun. 14, 1988

[54] MEDICAL PATCHES AND PROCESSES FOR PRODUCING SAME

[75] Inventors: Michael Szycher, Lynnfield; Jonathan L. Rolfe, Easton, both of Mass.

[73] Assignee: Thermedics, Inc., Woburn, Mass.

[21] Appl. No.: 53,496

[22] Filed: May 11, 1987

Related U.S. Application Data

[63] Continuation of Ser. No. 826,273, Feb. 5, 1986, abandoned, which is a continuation-in-part of Ser. No. 726,809, Apr. 25, 1985, abandoned, which is a continuation-in-part of Ser. No. 670,810, Nov. 13, 1984, Pat. No. 4,614,787.

[51] Int. Cl.[4] ............... B05D 3/02; B32B 7/00; D04B 1/00; C09U 7/02
[52] U.S. Cl. ............... 428/254; 427/2; 427/389.9; 428/253; 428/343; 428/354; 428/913; 604/304
[58] Field of Search ............... 427/2, 389.9; 428/253, 428/254, 343, 354, 913; 604/304

[56] References Cited

U.S. PATENT DOCUMENTS

| | | | |
|---|---|---|---|
| 3,062,210 | 11/1962 | Scholl | 128/156 |
| 3,342,183 | 9/1967 | Edenbaum | 128/268 |
| 3,374,134 | 3/1968 | Waldman | 156/239 |
| 3,526,224 | 9/1970 | Potts | 128/156 |
| 3,567,119 | 3/1971 | Wilbert et al. | 239/6 |
| 3,570,482 | 3/1971 | Emoto et al. | 128/156 |
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,734,097 | 5/1973 | Zaffaroni | 128/268 |
| 3,742,951 | 7/1973 | Zaffaroni | 128/268 |
| 3,842,832 | 10/1974 | Wideman et al. | 128/169 |
| 3,870,593 | 3/1975 | Elton et al. | 161/159 |
| 3,881,473 | 5/1975 | Corvi et al. | 128/90 |
| 3,949,742 | 4/1976 | Nowakowski | 128/155 |
| 3,975,567 | 8/1976 | Lock | 428/315 |
| 4,034,751 | 7/1977 | Hung | 428/292 X |
| 4,038,239 | 7/1977 | Coyner et al. | 528/75 |
| 4,051,848 | 10/1977 | Levine | 128/156 |
| 4,144,317 | 3/1979 | Higuchi et al. | 424/21 |
| 4,156,067 | 5/1979 | Gould | 528/73 |
| 4,189,467 | 2/1980 | von Bittera et al. | 424/14 |
| 4,209,605 | 1/1980 | Hoy et al. | 528/54 |
| 4,215,684 | 8/1980 | Westip | 128/156 |
| 4,233,969 | 11/1980 | Lock et al. | 128/156 |
| 4,236,550 | 12/1980 | Braun et al. | 139/421 |
| 4,264,757 | 4/1981 | Park | 528/75 |

(List continued on next page.)

FOREIGN PATENT DOCUMENTS

| | | |
|---|---|---|
| 273966 | 3/1967 | Australia . |
| 0114581 | 1/1984 | European Pat. Off. . |
| 1476894 | 4/1975 | United Kingdom . |
| 2093702 | 9/1982 | United Kingdom . |

Primary Examiner—Michael R. Lusignan
Attorney, Agent, or Firm—Lorusso & Loud

[57] ABSTRACT

A layer or member particularly useful as part of a medical patch such as an anisotropic wound dressing, a transdermal skin patch or an incise medical drape and the processes for forming such a member. The member is comprised of a crosslinked thermoset aliphatic polyurethane elastomer. The elastomer is the reaction product of (1) isophorone diisocyanate, (2) a macroglycol and (3) a chain terminator having both hydroxyl and vinyl functional groups. Polycarbonate glycols or polyetherglycols having a molecular weight of 500-2500 Daltons are preferred macroglycols and isophorone diamine is a preferred chain terminator. In one embodiment, a member or polyurethane layer for use as a wound dressing or an incise medical drape is produced by applying a film-forming solution or dispersion as a thin film to a supporting release paper and treating the film to drive off the liquids and to activate a crosslinker. In another embodiment, a member for an anisotropic medical patch is produced by sandwiching a knitted reinforcing fabric in the elastomer. When used as a transdermal skin patch or a drug dispensing wound dressing, a layer of drug dispensing film containing pharmacoactive agents may be applied to the medical patch, and when appropriate, the medical patch may be coated with a pressure sensitive adhesive.

61 Claims, 2 Drawing Sheets

U.S. PATENT DOCUMENTS

| | | | |
|---|---|---|---|
| 4,306,551 | 12/1981 | Hymes et al. | 128/156 |
| 4,307,717 | 12/1981 | Hymes et al. | 128/156 |
| 4,308,184 | 12/1981 | Thoma et al. | 428/904 X |
| 4,321,117 | 3/1982 | Kaetsu et al. | 204/159 |
| 4,331,135 | 5/1982 | Westip | 128/156 |
| 4,336,243 | 6/1982 | Sanvordeker | 424/28 |
| 4,340,043 | 7/1982 | Seymour | 128/132 |
| 4,391,106 | 7/1983 | Schefer et al. | 66/193 |
| 4,411,754 | 10/1983 | Kaetsu et al. | 204/159.15 |
| 4,425,395 | 1/1984 | Negishi et al. | 427/389.9 |
| 4,447,590 | 3/1984 | Szycher | 528/76 |
| 4,460,369 | 7/1984 | Seymour | 604/897 |
| 4,476,697 | 10/1984 | Schafer et al. | 66/193 |
| 4,483,759 | 11/1984 | Szycher et al. | 204/159.24 |
| 4,496,535 | 1/1985 | Gould et al. | 424/19 |

MEDICAL PATCHES AND PROCESSES FOR PRODUCING SAME

CROSS-REFERENCE TO A RELATED APPLICATION

This is a continuation of co-pending application Ser. No. 826,273 filed on Feb. 5, 1986, now abandoned.

Application Ser. No. 826,273 is a continuation-in-part of prior application U.S. Ser. No. 726,809, filed Apr. 25, 1985, entitled "Anisotropic Wound Dressing", now abandoned, which is a continuation-in-part of prior application U.S. Ser. No. 670,810, filed Nov. 13, 1984, entitled "Drug Dispensing Wound Dressing", now U.S. Pat. No. 4,614,787, patented Sept. 30, 1986.

BACKGROUND OF THE INVENTION

There has long been a need for a medical patch particularly for use as a wound dressing which is thin, soft, pliable and elastic, yet high in water vapor transmission and abrasion resistance and which does not promote the growth of bacteria.

Presently available bandages made of materials such as cotton are undesirable because they retain water, serve as growth media for bacteria, and soak up tissue pieces and blood which clots, causing adhesion to the wound and trauma during removal.

Bandages made of plastic materials to decrease the undesirable water absorption of cotton wound dressings are available. Unfortunately, problems due to lack of oxygen transmission through the plastic result from the use of many plastic materials. Indeed, holes are punched through the plastic covering to allow the transmission of some oxygen to the skin below. Such constructions do not provide a barrier to low surface tension aqueous solutions, e.g. washing-up liquid (which will also allow bacteria to penetrate). Silicone coatings have been applied to the area of the bandage adjacent to the wound to prevent adhesion. These coatings did not significantly decrease the problem of the bandage sticking to the wound, and do nothing to reduce the blocked oxygen problem.

In further attempts to overcome the adhesion and permeability problems, polyurethane and other plastic dressings were tried. For example, U.S. Pat. No. 3,975,567 to Lock discloses a pressure and heat-treated polyurethane foam which is lyophilic and U.S. Pat. No. 3,870,593 to Elton et al. discloses a polymeric film comprised of finely divided particles of non-hygroscopic inorganic salt dispersed in a suitable polymer.

Other polyurethanes which polymerize upon exposure to ultraviolet light were also developed. The majority of these UV-curable polyurethanes were designed for use as orthopedic casts, for example, U.S. Pat. No. 4,209,605 discloses such a cast. None of these compositions managed to combine the properties of softness, oxygen and water vapor permeability, flexibility, and thixotropy.

The desired material for use as a wound dressing or bandage must be permeable to water vapor, but not permeable to liquid water, microorganisms and particles of dirt. The material may also be anisotropic, by which is meant that the fabric stretches more in one direction than in the other. This characteristic allows the dressing to stretch in the direction of the skin to which it is applied and allows for easy application.

The material should also be thin so that the dressing is not easily bumped or displaced by contact with outside sources. Other bandages which use a knitted fabric result in a very voluminous bandage. See, for example, U.S. Pat. No. 4,236,550 to Braun et al. and U.S. Pat. No. 4,391,106 to Schafer et al. Thinner wound dressings presently available and formed of polyurethane often require two or more trained medical personnel for proper application because of their thinness, elasticity and tendency to stick to themselves during application.

SUMMARY OF THE INVENTION

Prior application, U.S. Ser. No. 726,809, discloses a wound dressing formed of an ultrathin polyurethane membrane which allows light and oxygen to reach the wound while serving as a barrier to bacteria. The dressing comprises a textile reinforcement fabric sandwiched within a layer of crosslinked aliphatic polyurethane material. The fabric enables the wound dressing to be made thin and yet be anisotropic and strong.

This invention is directed to medical patches particularly useful as a wound dressing but also useful as a transdermal skin patch or an incise medical drape, and to an efficient process for making members for such medical patches. The member itself is comprised of a crosslinked thermoset aliphatic polyurethane elastomer. In one embodiment, a film-forming liquid such as a dispersion or a solution containing a polyurethane elastomer and a crosslinker is utilized to form a thin film on release paper, which is then treated to evaporate volatile liquids and to activate the crosslinker. The treatment produces a member or layer for a medical patch of a highly crosslinked, thermoset aliphatic polyurethane elastomer with the desired qualities for a wound dressing, a transdermal skin patch, or an incise medical drape. In another embodiment, a film-forming liquid is applied to an open mesh, very porous reinforcing fabric in a one step coating process. As the fabric is drawn through the liquid, a film is formed on the fabric, with pellicles which fill the interstices of the fabric. The coated fabric is then treated to evaporate substantially all volatile liquids and to activate the crosslinker. The treatment produces a member or layer of a crosslinked, thermoset polyurethane reinforced by fabric with the desirable qualities for an anisotropic wound dressing or an anisotropic transdermal skin patch.

It is therefore an object of the present invention to provide a process for forming a medical patch which is strong, yet flexible, and which medical patch when applied to the body conforms to the shape of the site of the application.

It is still a further object of the present invention to provide such a process for making a material for use in medical patches which is anisotropic and thin.

It is still a further object of the present invention to provide a process for making a material for a medical patch which can be easily formed and has sufficient support so that it retains its shape so that it can easily be applied to the body by one person in adverse circumstances.

It is still a further object of the present invention to provide a process for making a material for use as a member for a medical patch which is biocompatible and oxygen and water vapor permeable.

Another object of the invention is to provide a new polyurethane material which can be used in medical applications.

Yet another object of the present invention is to provide a member for use in a medical patch with improved properties.

The foregoing and other objects and features of the claimed invention will be understood by those skilled in the art from a reading of the description which follows.

DESCRIPTION OF THE PREFERRED EMBODIMENTS

Figure 1:
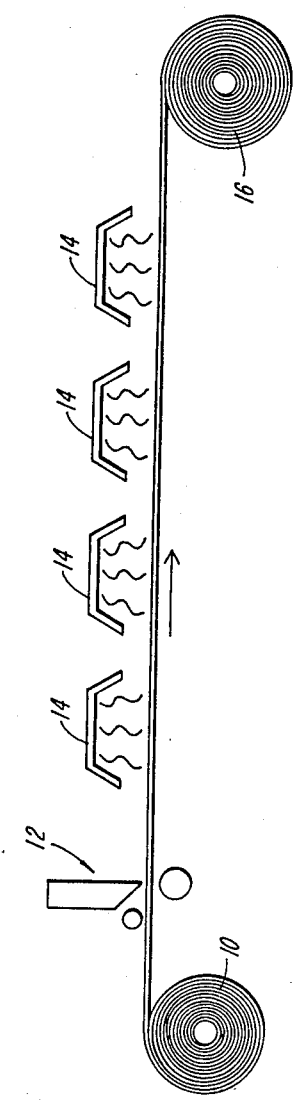
FIG. 1 is a schematic diagram of the process to form one embodiment of the present invention, a member or layer for use in an incise medical drape or a wound dressing.

At the outset, this invention is described in its broadest overall aspects with a more detailed description following.

The medical patches of the present invention comprise a crosslinked thermoset aliphatic polyurethane elastomer member or layer. In one embodiment, a film-forming liquid is prepared containing a polyurethane elastomer and a crosslinker. The liquid, which is preferably a solution or dispersion, is applied as a thin film of elastomer to supporting release paper, and the film is used to form a medical patch particularly useful as a wound dressing or an incise medical drape. A layer of drug dispensing film may be applied to the treated product and, where appropriate, one side may be coated with a pressure sensitive adhesive.

In another embodiment, a medical patch useful as an anisotropic wound dressing or transdermal skin patch is formed when an open mesh knitted fabric is drawn through the film-forming liquid. A film coats the fabric fibers and fills the interstices of the fabric. The coated fabric is treated to evaporate volatile liquids and to activate the crosslinker. The treatment produces a crosslinked thermoset polyurethane member with a reinforcing fabric support. A thin drug dispensing layer or film may be applied to the member and, where appropriate, one side of the member may be provided with a pressure sensitive adhesive. An optional prerinse of the reinforcing fabric is preferred.

Any of several non-thermoplastic aliphatic polyurethane elastomers are suitable to prepare the member for the medical patch of this invention. A preferred formulation is the reaction product of isophorone diisocyanate and a macroglycol which results in an isocyanate terminated prepolymer. The prepolymer is then reacted with a chain terminator to form an aliphatic polyurethane elastomer.

The isophorone diisocyanate (IPDI) used in the present invention is an aliphatic compound having the following formula:

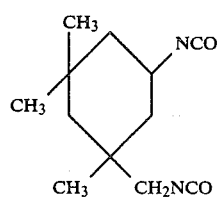

IPDI is utilized in the present invention because it is a liquid at room temperature and thus, easily coats the fabric if it is used. The compound reacts quickly with the other compounds of the elastomer and can readily be obtained commercially.

A preferred macroglycol for use in the present invention is a polycarbonate glycol having a molecular weight of 500–2500 Daltons, preferably 1500–2200 Daltons, and most preferably about 2000 Daltons, and having the following formula:

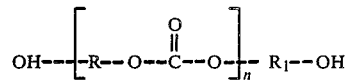

where R and $R_1$ are aliphatic linear chains of 1–20 carbons and $n$ is an integer from 5 to 25. Duracarb 122, a general trade designation of Pittsburg Plateglass Company for polycarbonate glycol, is such a macroglycol and may be used in this invention. Use of such a macroglycol is preferred because polyurethane formed from it has high abrasion resistance and high tear resistance. Another preferred high molecular weight glycol is polytetramethylene ether glycol (PTMEG). As used herein, the term "macroglycol" has reference to any glycol having a molecular weight in excess of 500 Daltons.

The chain terminator used in formulating the layer or member of the invention should have both hydroxyl and vinyl functional groups and is preferably an acrylic compound such as hydroxyethyl acrylate or hydroxyethyl methacrylate. Isophorone diamine (IPDA) is a preferred chain terminator because it is liquid at room temperature and it reacts quickly with the other components. The resulting polyurethane elastomer film has the desired physical properties of high tensile strength, high elongation and high tear resistance. Another suitable chain terminator is hydroxyethyl methacrylate (HEMA).

The diisocyanate, macroglycol and chain terminator are reacted in approximately stoichiometric amounts, i.e., in the approximate ratio of 2 moles (2.0 equiv.) isophorone diisocyanate to 1 mole (1.0 equiv.) macroglycol to 1 mole (1.0 equiv.) chain terminator. At the end of the reaction between the prepolymer and the chain terminator, free isocyanate is monitored by infrared spectrophotometry and, if necessary, additional small amounts of the chain terminator may be added to scavenge any remaining isocyanate. It is important that the low molecular weight monomers present in the composition be reacted prior to contact with the skin so that only compounds with molecular weights of 1500–5000 Daltons are present. The high molecular weight compounds do not leach out of the medical patch into the underlying tissue and are therefore non-toxic.

An antioxidant such as tetrakis (methylene 3,5-di-tert-butyl-4-hydroxyhydrocinnamate) may be added.

A polyurethane catalyst such as dioctyl tin dilaurate, N-methyl morpholine, trimethylamine, triethylamine, zinc octoate, or dibutyl tin dilaurate is added to both the reaction medium in which the prepolymer is formed and the reaction medium in which the prepolymer is reacted with the chain terminator.

The layer or member comprising the above-described polyurethane elastomer is used in medical patches which may be a wound dressing (with or without drugs), an incise medical drape or a transdermal drug releasing system.

An incise medical drape is placed over an area of the body where an incision will be made. Any fabric in the drape would make it harder to cut through the drape to make the incision. Furthermore, any loose threads from an incision could get into the open incision and raise the risk of infection. The medical patch of this invention, when formed without the reinforcing fabric, would enable the user to make a clean, easy cut into the body.

To form the member or layer for the medical patch, a film-forming liquid is prepared containing the above polyurethane and a suitable crosslinker. Use of a crosslinker permits high heat input for drying so that fast drying time of the film is accomplished. Also, the resulting member or layer, because it is highly crosslinked and therefore is thermoset, is less sensitive than non-crosslinked materials to organic solvents such as alcohol frequently used for swabbing in operating rooms and clinical settings—i.e., it will not soften or become sticky. An acrylic crosslinker may be used, and a preferred crosslinker is CARBOSET 525, a trade designation of B.F. Goodrich Chemical Company for a heat-reactive polyacrylate. This crosslinker should be added to the film-forming liquid soon before its application to a release paper or reinforcing fabric because the crosslinker has a short shelf life. Moreover, in the embodiment of this invention where the polyurethane elastomer is formed on a reinforcing fabric, a crosslinker must be added to the coating dispersion or solution before this liquid is applied to the fabric because, without crosslinker, the thin pellicles formed on the fabric by the coating liquid will otherwise melt from the drying heat temperature.

The film-forming liquid may be a solution including the polyurethane elastomer and crosslinker dissolved in an organic solvent. Alternatively, the film-forming liquid may be a dispersion including the elastomer and crosslinker dispersed in water.

As an example of a solution-type film-forming liquid according to the invention, a solution is prepared having about 10% solute in 90% solvent by weight. The 10% solute is comprised of 9% of the above polyurethane elastomer and 1% crosslinker such as CARBOSET 525. The solute is mixed with a solvent having a composition of about 90% tetrahydrofuran (THF) and 10% M-Pyrrol. (M-Pyrrol is a trade designation of GAF, Inc., of New Jersey for N-methyl-2-pyrrolidone, a slow-drying anti-blushing solvent.) Methylene chloride may be used as an alternative for THF if a non-flammable solution is desired.

The above-described solution of a dissolved polyurethane elastomer and a crosslinker in a solvent for both is formed as a thin film, e.g. 0.05–0.10 mm, on release paper by use of a rod coater or other coating device. The release paper does not form any part of the completed medical patch but provides support for the film during the curing process. The film is then treated to evaporate the solvents and to activate the crosslinker. Preferably, the film is treated with infrared heaters 14 such as five 500-watt quartz lamps each supplying 20 watts per inch output of energy to the film as it passes the lamps. The film is thus treated to 100 watts per inch at a speed of 1 yard per minute or less. As the film is treated, its temperature rises from approximately 120° F. to a maximum of approximately 325° F. At approximately 125° F., the solvent is evaporated. The higher temperature causes the crosslinker to be activated which thermosets the polyurethane elastomer and produces the member or layer which will be used in the medical patch of this invention.

As shown in FIG. 1, release paper 10 is coated with the film-forming liquid of polyurethane elastomer and crosslinker at point 12, then treated, preferably with infrared heaters 14. The crosslinked, aliphatic, polyurethane elastomer film backed by the release paper 16, may then be rolled and stored until used.

The medical patch comprising a member or layer of this crosslinked polyurethane elastomer is clear, soft and elastic. The thickness of the polyurethane member is 0.25 mm or less and preferably is about 0.05–0.10 mm. The resulting product is thin, oxygen and water vapor permeable, strong, does not wrinkle, and therefore, keeps its shape. Because there is no gauze, bacteria buildup is prevented.

A drug dispensing member, as described in copending application, U.S. Ser. No. 768,623, filed Aug. 23, 1985, entitled "Drug Release System", may be applied to the member or layer in a medical patch where appropriate or desired.

Any pressure sensitive adhesive conventionally used for wound dressings or bandages, e.g. a polyacrylate adhesive or a polyvinylethyl ether blend adhesive, may be spread over either the drug dispensing layer or, if no drug dispensing layer is used, over the the member or layer if it is to be used as a wound dressing. A release paper or plastic film is then applied over the exposed surface of the adhesive.

In another embodiment, the polyurethane member or layer of this invention can be used in a medical patch as an anisotropic wound dressing or anisotropic transdermal skin patch. This medical patch comprises a member or layer of an open mesh reinforcing fabric sandwiched in a polyurethane elastomer. A one step coating process for making this medical patch comprises providing an open mesh knitted fabric which is drawn through the film-forming liquid containing the polyurethane elastomer and crosslinker referred to hereinabove. The liquid coats the fabric fibers and fills the interstices of the fabric. The coated fabric is treated to evaporate the volatile liquids present, (organic solvents and/or water), and to activate the crosslinker. The complete medical patch may contain a thin drug dispensing layer or film which is applied to the fabric-reinforced polyurethane member. In addition, where appropriate, one side of the medical patch may be provided with a pressure sensitive adhesive.

The open mesh knitted fabric is used as a reinforcement. The term "knitted" is intended to describe the process to form textile material by interlacing yarn or threads in a series of connected loops with needles. The support fabric can be made out of any textile material, such as a polyester. Present cost considerations, however, make nylon the preferred choice. A desirable fabric is a warp knit 15 denier nylon tricot, heat set material. One such fabric is sold by Gehrring Textiles, New York, N.Y., and is formed from Nylon 6 yarns. Any fabric of the proper geometry, however, which is biocompatible may be used.

The preferred knitted fabric has the following characteristics. The openings in the fabric are hexagonal, of a size ranging from about 0.5 mm to 4 mm across, although preferably they are about 2 mm across in size. The fabric is knitted from yarns having a diameter in the range of about 0.025–0.203 mm, although preferably with a diameter of about 0.1 mm. The term "yarn" as used herein is intended to describe both yarns formed from monofilaments or single fibers or yarns formed from filaments twisted together. The yarn itself need only have modest elongation properties. The stretch characteristic of the fabric is achieved by the mechanical processing and geometry.

The small thread to large open space ratio in the fabric is considered important because it minimizes the obstruction of light and moisture, provides high tear characteristics and suppleness and contributes to the anisotropic tendencies. As stated above, the diameter of the thread will range from about 0.025–0.203 mm. The size of the void area measured as the distance across the openings will range from about 0.5 to 4.0 mm. In a preferred embodiment, the ratio of the diameter of the thread to the size of the void area is then 0.1:2, or approximately 5% thread to 95% void area.

Figure 2:
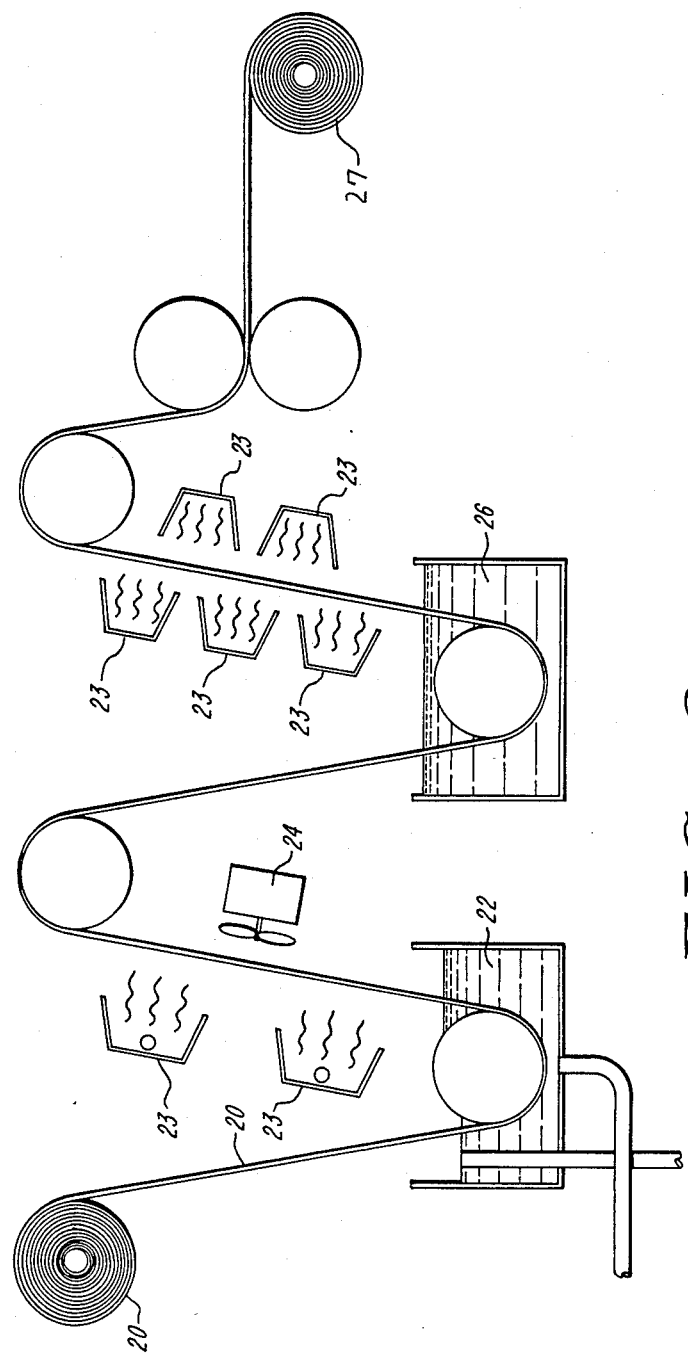
FIG. 2 is a schematic diagram of the process to form another embodiment of the present invention, a member or layer for use in an anisotropic wound dressing or an anisotropic transdermal skin patch.

As shown in FIG. 2, the above-described fabric 20 is preferably drawn through a rinse solution, 22, before the polyurethane elastomer film is applied. A desirable rinse is a basic solution, which leaves no residue when it evaporates. A preferred solution is $NH_4OH$, ammonium hydroxide, at concentrations of about 2% by weight. Use of a rinse step produces a better film by preventing voids in the film which are caused by oil, lint, and dust on the fabric. Unless eliminated, these pieces of lint and dust act as void-forming nuclei which break, or form small holes in, the pellicles of the solution formed around them. After the rinse, the solution is evaporated from the fabric, preferably by infrared heaters, 23, and/or drying fans, 24.

The above-described fabric is then drawn through the solution or dispersion containing the above-described polyurethane elastomer and crosslinker, 26, with a speed sufficient to coat the yarns or fibers of the fabric and to fill the interstices. The speed may, for example, be 1–3 feet per minute. The elastomer coated fabric is treated, preferably with infrared heaters, 23, to evaporate the solvents and/or water and to activate the crosslinker. The treatment produces a highly crosslinked polyurethane elastomer member reinforced by fabric which may be formed into a roll 27 for later use in a medical patch such as an anisotropic wound dressing or anisotropic transdermal skin patch.

When used as a drug dispensing system, the medical patch may comprise a thin drug dispensing layer or film which is applied to the member. Where appropriate, the member may be provided with a pressure sensitive adhesive, as described above.

The invention is further illustrated by the following non-limiting example.

EXAMPLE

Referring to FIG. 2, an open mesh knitted fabric, Nylon 6, is shown at 20. Force is applied on the fabric to pull it at a speed of 1–3 feet per minute. The fabric first passes through a bath, 22, comprising a rinse solution of 2% ammonium hydroxide in water. The rinse solution is evaporated from the fabric by infrared lamps 23 or fans 24.

Continuing at the same approximate rate of speed, the fabric is pulled through bath 26 which comprises a 10% solution of polymer in 90% solvent system, as follows:
  9% polyurethane
    2 moles (2.0 equiv.) IPDI
    1 mole (1.0 equiv.) PTMEG 2000
    1 mole (1.0 equiv.) IPDA
  1% CARBOSET 525
  81% tetrahydrofuran
  9% N-methyl-2- pyrrolidone The coated fabric is passed by infrared lamps at the same approximate rate of speed to evaporate the solution and activate the crosslinker. Preferably, the fabric is 4 inches away from the lamp and the temperature of the material to be dried and cured is no greater than 95° C. with 500 watts per foot of lamps used.

The resulting product is a highly crosslinked polyurethane elasomer member reinforced by fabric. The member may be rolled, 27, for later use.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A process for forming a layer or member particularly useful as part of a medical patch such as an anisotropic wound dressing, comprising the steps of:
   (a) providing a film-forming liquid consisting essentially of a polyurethane and a crosslinker;
   (b) passing an anisotropic knitted reinforcing fabric defining a network of open interstices having a void area between the range of about 0.5 mm to 4 mm across and formed of yarns having a diameter in the range of about 0.025 to 0.203 mm through said solution with sufficient speed to coat the yarns of said fabric and form a film which fills the interstices of the fabric;
   (c) treating said coated fabric to drive off volatile liquids remaining in said coating and to activate the crosslinker to form a member suitable for a medical patch comprising a fabric encapsulated by and embedded in a crosslinked polyurethane elastomer member suitable for a medical patch.

2. The process of claim 1 including, prior to applying said film-forming liquid to said fabric, the step of rinsing said fabric with a basic solution of remove oil, lint and dust.

3. The process of claim 2 wherein the basic solution of the rinse step is ammonium hydroxide.

4. The process of claim 1 wherein the void area of said knitted reinforcing fabric is about 2 mm across.

5. The process of claim 1 wherein the thickness of the polyurethane in the area of the member where the polyurethane fills the interstices of the knitted reinforcing fabric is about 0.01 mm.

6. The process of claim 1 wherein said knitted reinforcing fabric is formed from yarns having a diameter of about 0.1 mm.

7. The process of claim 1 wherein said knitted reinforcing fabric is a material formed from Nylon 6 yarns.

8. The process of claim 1 wherein said polyurethane elastomer is the reaction product of
   (a) a diisocyanate;
   (b) a macroglycol; and
   (c) a chain terminator.

9. The process of claim 8 wherein said polyurethane elastomer is the reaction product of:
   (a) isophorone diisocyanate;
   (b) a macroglycol selected from the group consisting of polytetramethylene ether glycol and polycarbonate glycol; and (c) isophorone diamine.

10. The process of claim 1 wherein said film-forming liquid comprises a solution of a dissolved polyurethane elastomer and a crosslinker in solvents for both.

11. The process of claim 10 wherein said solution consists of about 10% solute in 90% solvent by weight, said solute comprising about 90% polyurethane elastomer and about 10% crosslinker, and said solvent consisting of about 90% tetrahydrofuran and 10% N-methyl-2-pyrrolidone.

12. The process of claim 10 wherein said crosslinker is a heat-reactive polyacrylate.

13. The process of claim 1 further comprising applying a coating of a pressure sensitive adhesive on one surface of said member produced in steps (a) through (c).

14. The process of claim 1 further comprising applying a layer or film of material which disperses a pharmacoactive agent to the elastomer coated fabric obtained in steps (a) through (c).

15. A member or layer particularly useful for a medical patch such as an anisotropic wound dressing a prepared by a process comprising the steps of:
   (a) providing a film-forming liquid consisting essentially of a polyurethane elastomer and a crosslinker;
   (b) passing an anisotropic knitted reinforcing fabric defining a network of oepn interstices having a void area between the range of about 0.5 mm to 4 mm across and formed of yarns having a diameter in the range of about 0.025 to 0.203 mm through said film-forming liquid with sufficient speed to coat the yarns of the fabric and form a film which fills the interstices of the fabric;
   (c) Treating said coated fabric to drive off volatile liquids and to activate the crosslinker to form a member comprising a crosslinked polyurethane encapsulated fabric.

16. The member of claim 15 wherein the void area of said knitted reinforcing fabric is about 2 mm across.

17. The member of claim 15 wherein the thickness of said polyurethane in the area of the member where the polyurethane fills the interstices of the knitted reinforcing fabric is about 0.01 mm.

18. The member of claim 15 wherein said knitted reinforcing fabric is formed form yarns having a diameter of about 0.1 mm.

19. The member of claim 15 wherein said knitted reinforcing fabric is a material formed from Nylon 6 yarns.

20. The member of claim 15 wherein said polyurethane elastomer is the reaction product of
   (a) a diisocyanate;
   (b) a macroglycol; and
   (c) a chain terminator.

21. The member of claim 20 wherein said polyurethane elastomer is the reaction product of:
   (a) isophorone diisocyanate;
   (b) a macroglycol selected from the group consisting of polytetramethylene ether glycol and polycarbonate glycol; and
   (c) isophorone diamine.

22. The member of claim 15 wherein said film-forming liquid comprises a solution of a dissolved polyurethane elastomer and a crosslinker in solvents for both, said solution consisting of about 10% solute in 90% solvent by weight, said solute comprising about 90% polyurethane elastomer and 10% crosslinker, and said solvent consisting of about 90% tetrahydrofuran and 10% N-methyl-2-pyrrolidone.

23. The member of claim 22 wherein said crosslinker is a heat-reactive polyacrylate.

24. The member of claim 15 wherein said process further comprises applying a layer or film of material which disperses a pharmacoactive agent to the polyurethane coated fabric obtained in steps (a) through (c).

25. The member of claim 15 further comprising a layer of pressure sensitive adhesive on one side of the member obtained in steps (a) through (c).

26. A polyurethane elastomer for forming a member or layer particularly useful for a medical patch such as a wound dressing or an incise medical drape consisting essentially of the reaction product of:
   (a) 2.0 equivalent weight isophorone diisocyanate;
   (b) 1.0 equivalent weight of a macroglycol selected from the group consisting of polytetramethylene ether glycol and polycarbonate glycol; and
   (c) 1.0 equivalent weight isophorone diamine.

27. The elastomer of claim 26 further comprising a crosslinker in sufficient amounts and further subjected to treatment to activate said crosslinker so that a 5–10% crosslinked polyurethane material is formed.

28. A process for forming a member or layer particularly useful as a medical patch such as a wound dressing or incise medical drape comprising the steps of:
   (a) providing a film-forming liquid consisting essentially of a polyurethane elastomer and a crosslinker;
   (b) applying said film-forming liquid to a release paper in a thin film;
   (c) treating said film to drive off volatile liquids and to activate the crosslinker to form a crosslinked polyurethane elastomer member.

29. The process of claim 28 wherein said polyurethane elastomer is the reaction product of
   (a) a diisocyanate;
   (b) a macroglycol; and
   (c) a chain terminator.

30. The process of claim 28 wherein said polyurethane elastomer is the reaction product of:
   (a) isophorone diisocyanate;
   (b) a macroglycol selected from the group consisting of polytetramethylene ether glycol and polycarbonate glycol; and
   (c) isophorone diamine.

31. The process of claim 28 wherein said film-forming liquid comprises a solution of a dissolved polyurethane elastomer and a crosslinker in solvents for both, said solution consisting of about 10% solute in 90% solvent by weight, said solute comprising about 90% polyurethane elastomer and 10% crosslinker and said solvent consisting or about 90% tetrahydrofuran and 10% N-methyl-2-pyrrolidone.

32. The process of claim 31 wherein said crosslinker is a heat-reactive polyacrylate.

33. The process of claim 28 wherein said treatment step comprises exposing the film to infrared heaters.

34. The process of claim 28 further comprising applying a coating of a pressure sensitive adhesive on one surface of said member obtained in steps (a) through (c).

35. The process of claim 28 further comprising applying a layer or film of material which disperses a pharmacoactive agent to the polyurethane member obtained in steps (a) through (c).

36. A process for forming a layer or member particularly useful as part of a medical patch such as an anisotropic wound dressing comprising the steps of:
  (a) provding a film-forming liquid consisting essentially of a biocompatible polyurethane;
  (b) passing an anisotropic knitted reinforcing fabric defining a network of open interstices having a void area between the range of about 0.5 mm to 4 mm across and formed of yarns having a diameter in the range of about 0.025 to 0.203 mm through said solution with sufficient speed to coat the yarns of said fabric and form a film which fills the interstices of the fabric;
  (c) treating said coated fabric to drive off volatile liquids remaining in said film to form a member suitable for a medical patch.

37. The process of claim 36 including, prior to applying said film-forming liquid to said fabric, the step of rinsing said fabric with a basic solution to remove oil, lint and dust.

38. The process of claim 37 wherein the basic solution of the rinse step is ammonium hydroxide.

39. The process of claim 36 wherein the void area of said knitted reinforcing fabric is about 2 mm across.

40. The process of claim 36 wherien the thickness of the polyurethane in the area of the member where the polyurethane fills the interstices of the knitted reinforcing fabric is about 0.01 mm.

41. The process of claim 36 wherein said knitted reinforcing fabric is formed from yarns having a diameter of about 0.1 mm.

42. The process of claim 36 wherein said knitted reinforcing fabric is a material formed from Nylon 6 yarns.

43. The process of claim 36 wherien said polyurethane elastomer is the reaction product of:
  (a) a diisocyanate;
  (b) a macroglycol; and
  (c) a chain terminator;
and said film-forming liquid further comprises a crosslinker.

44. The process of claim 43 wherein said polyurethane elastomer is the reaction product of:
  (a) isophorone diisocyanate;
  (b) a macroglycol selected from the group consisting of polytetramethylene ether glycol and polycarbonate glycol; and
  (c) isophorone diamine.

45. The process of claim 36 wherein said film-forming liquid consisting essentially of a solution of a dissolved polyurethane elastomer and a crosslinker in solvents for both.

46. The process of claim 45 wherein said solution consists of about 10% solute in 90% sollvent by weight, said solute comprising about 90% polyurethane elastomer and about 10% crosslinker, and said solvent consisting of about 90% tetrahydrofuran and 10% N-methyl-2-pyrrolidone.

47. The process of claim 45 wherein said crosslinker is a heat-reactive polyacrylate.

48. The process of claim 36 further comprising applying a coating of a pressure sensitive adhesive on one surface of said member produced in steps (a) through (c).

49. The process of claim 36 further comprising applying a layer or film of material which disperses a pharmacoactive agent to the elastomer coated fabric obtained in steps (a) through (c).

50. A member or layer particularly useful for a medical patch such as an anisotropic wound dressing prepared by a process comprising the steps of:
  (a) providing a film-forming liquid consisting essentially of a biocompatible polyurethane elastomer;
  (b) passing a knitted reinforcing fabric defining a network of open interstices having a void area between the range of about 0.5 mm to 4 mm across and formed of yarns having a diameter in the range of about 0.025 to 0.203 mm through said film-forming liquid with sufficient speed to coat the yarns of the fabric and form a film which fills the interstices of the fabric;
  (c) treating said coated fabric to drive off volatile liquids to form the member.

51. The member of claim 50 wherein the void area of said knitted reinforcing fabric is about 2 mm across.

52. The member of claim 50 wherien the thickness of said polyurethane in the area of the member where the polyurethane fills the interstices of the knitted reinforcing fabric is about 0.01 mm.

53. The member of claim 50 wherein the thickness of said film is about 0.01 mm.

54. The member of claim 50 wherein said knitted reinforcing fabric is formed from yarns having a diameter of about 0.1 mm.

55. The member of claim 50 wherein said knitted reinforcing fabric is a material fromed from Nylon 6 yarns.

56. The member of claim 50 wherein said polyurethane elastomer is the reaction product of:
  (a) a diisocyanate;
  (b) a macroglycol; and
  (c) a chain terminator;
and the film-forming liquid further comprises a crosslinker.

57. The member of claim 56 wherein said polyurethane elastomer is the reaction product of:
  (a) isophorone diisocyanate;
  (b) a macroglycol selected from the group consisting of polytetramethylene ether glycol and polycarbonate glycol; and
  (c) isophorone diamine.

58. The member of claim 50 wherein said film-forming liquid consisting essentially of a solution of a dissolved polyurethane elastomer and a crosslinker in solvents for both, said solution consisting of about 10% solute in 90% solvent by weight, said solute comprising about 90% polyurethane elastomer and 10% crosslinker, and said solvent consisting of about 90% tetrahydrofuran and 10% N-methyl-2-pyrrolidone.

59. The member of claim 58 wherein said crosslinker is a heat-reactive polyacrylate.

60. The member of claim 50 wherein said process further comprises applying a layer of film of material which disperses a pharmacoactive agent to the polyurethane coated fabric obtained in steps (a) through (c).

61. The member of claim 50 further comprising a layer of pressure sensitive adhesive on one side of the member obtained in steps (a) through (c).

* * * * *